United States Patent
Derain

(10) Patent No.: US 9,198,998 B2
(45) Date of Patent: Dec. 1, 2015

(54) COMPOSITION CONTAINING A CELLULOSE, A VEGETABLE OIL AND A VOLATILE SOLVENT, AND USE THEREOF AS A DRESSING

(75) Inventor: Nathalie Derain, Prenois (FR)

(73) Assignee: LABORATORIES URGO, Chenove (FR)

( * ) Notice: Subject to any disclaimer, the term of this patent is extended or adjusted under 35 U.S.C. 154(b) by 0 days.

(21) Appl. No.: 14/007,562

(22) PCT Filed: Mar. 23, 2012

(86) PCT No.: PCT/FR2012/050604
§ 371 (c)(1),
(2), (4) Date: Jan. 7, 2014

(87) PCT Pub. No.: WO2012/131238
PCT Pub. Date: Oct. 4, 2012

(65) Prior Publication Data
US 2014/0154188 A1    Jun. 5, 2014

(30) Foreign Application Priority Data
Mar. 25, 2011 (FR) ...................................... 11 52513

(51) Int. Cl.
| | | |
|---|---|---|
| *A61K 8/02* | (2006.01) | |
| *A61L 26/00* | (2006.01) | |
| *A61K 8/34* | (2006.01) | |
| *A61K 8/37* | (2006.01) | |
| *A61K 8/73* | (2006.01) | |
| *A61K 8/92* | (2006.01) | |
| *A61K 9/70* | (2006.01) | |
| *A61Q 19/00* | (2006.01) | |
| *A61K 47/38* | (2006.01) | |
| *A61K 47/44* | (2006.01) | |

(52) U.S. Cl.
CPC ............... *A61L 26/0023* (2013.01); *A61K 8/34* (2013.01); *A61K 8/37* (2013.01); *A61K 8/731* (2013.01); *A61K 8/922* (2013.01); *A61K 9/7015* (2013.01); *A61K 47/38* (2013.01); *A61K 47/44* (2013.01); *A61L 26/00* (2013.01); *A61L 26/0057* (2013.01); *A61L 26/0066* (2013.01); *A61Q 19/00* (2013.01); *A61K 2800/10* (2013.01)

(58) Field of Classification Search
CPC ............ A61K 8/34; A61K 8/37; A61K 8/731; A61K 8/922; A61K 9/7015; A61K 2800/10; A61K 47/38; A61K 47/44; A61Q 19/00
See application file for complete search history.

(56) References Cited

U.S. PATENT DOCUMENTS

| | | | |
|---|---|---|---|
| 3,247,845 A * | 4/1966 | Kennedy | 602/54 |
| 5,433,950 A | 7/1995 | Popp | |
| 5,525,358 A | 6/1996 | Popp | |
| 6,337,076 B1 * | 1/2002 | Studin | 424/401 |
| 2007/0048355 A1 | 3/2007 | Perlman | |

FOREIGN PATENT DOCUMENTS

| | | |
|---|---|---|
| GB | 754844 | 8/1956 |
| GB | 795583 | 5/1958 |
| JP | 2008-273918 | 11/2008 |
| WO | WO 01/37782 | 5/2001 |

* cited by examiner

*Primary Examiner* — Lezah Roberts
*Assistant Examiner* — Nannette Holloman
(74) *Attorney, Agent, or Firm* — Hamre, Schumann, Mueller & Larson P.C.

(57) ABSTRACT

The present invention relates to a composition in the fluid form intended to form a dressing on the skin. This composition comprises from 6% to 12% by weight of the total weight of the composition of a cellulose derivative, from 5% to 15% by weight of the total weight of the composition of a vegetable oil, and a volatile solvent. The oil/cellulose ratio by weight is between 0.8 and 1.5.

This novel dressing base makes it possible to obtain a film on the skin having satisfactory resistances to water and to rubbing actions. The film is flexible and sufficiently comfortable, in particular when the dressing is applied to a fairly extensive area of the skin.

9 Claims, No Drawings

COMPOSITION CONTAINING A CELLULOSE, A VEGETABLE OIL AND A VOLATILE SOLVENT, AND USE THEREOF AS A DRESSING

The present invention relates to a fluid composition intended to be applied to the skin, comprising a cellulose derivative, a vegetable oil and a solvent for the said derivative which is volatile. Once applied to the skin, the volatile solvent evaporates and the composition forms a solid film which can advantageously be used as dressing for a wound.

"Liquid" dressings can be formulated in the aqueous phase or in the solvent phase. They are generally provided in the form of a fluid which is applied to the skin via an appropriate applicator, such as a spray, a brush, a spatula or a palette knife. The water or the solvent which they comprise evaporates on contact with the skin, so as to form a solid film which protects the skin, the constituents of which penetrate the skin in a very limited fashion. These dressings exhibit the advantage of protecting the tissues by preventing bacterial contamination while allowing them to breathe.

The liquid dressings formulated with water often take a long time to dry. They are easily destroyed as soon as the body comes into contact with water, with the result that dressings in the solvent phase, having better resistance to water but also to rubbing actions and to soaps, are preferred to them.

Liquid dressings based on nitrocellulose comprising an oil and a volatile solvent have already been described in the prior art.

For example, the formulations described in the application WO 2001/0037782 comprise collodion, oils and active agents. However, the applicant company has found that the amount of composition deposited on the skin is not sufficient to suitably cover the skin over a relatively large surface area and to form a dressing sufficiently thick to effectively protect damaged skin. The example in this document comprises 4.4% of nitrocellulose, 2.6% of castor oil and 10% of silicone oil. The applicant company was able to find that the film obtained after coating with this formulation using a brush is very thin and friable. The protective surface is mediocre and the film nonuniform.

The document JP 2008-273918 describes an analogous composition comprising 2-10% of nitrocellulose, 0.3-3% of castor oil and a silicone oil. The applicant company has demonstrated that the percentage of plasticizer is too low for the film formed to be flexible. The film obtained is brittle and has a tendency to crumble and to crack; it is unsightly and does not correctly protect the skin or the wound.

Finally, the document US 2007/004835 relates to a liquid dressing for small wounds or small cuts, in which provision is made to replace a portion of the solvents irritating to the skin (conventionally used in liquid dressings) with volatile alkanes. One of the examples provided comprises 3.85% by weight of nitrocellulose and 2% of castor oil. This document mentions that the amount of nitrocellulose can be from 3% to 7% by dry weight. The applicant company has been able to find that the nitrocellulose used in a small amount results in a film which is too thin to be protective.

A ready-for-use liquid dressing comprising nitrocellulose, castor oil, wheat germ oil, ethanol and ethyl acetate has been marketed under the reference Filmogel® Crevasses. It is applied using a brush or a spatula, in order to fill in and uniformly cover the crack. The product is applied to a very limited area of the skin. When an attempt is made to apply it to a broader area, the film deposited is nonuniform as the mixture is not easily spread.

The applicant company has thus wished to develop a film-forming liquid dressing which can satisfactorily cover a more extensive skin area while obtaining a continuous, flexible and comfortable film of sufficient thickness. The product of the invention can advantageously be applied to an area of the skin subject to tensioning or elongating movements, in particular at the joints.

The applicant company has discovered that the proportions of nitrocellulose and of vegetable oil have to be sufficiently high for the spreading of the liquid dressing over the skin over a broad area to be uniform and for the comfort of the dry film on the skin, once the solvent has evaporated, to be satisfactory.

The applicant company has thus prepared a novel dressing base having satisfactory resistance to water and satisfactory resistance to rubbing actions. In addition, the films are flexible and provide the user with sufficient comfort, in particular when the dressing is applied to a fairly extensive area of the skin. The dressings of the invention can be applied uniformly to a relatively extensive application area, typically greater than 1 $cm^2$, indeed even greater than 5 $cm^2$. The amount of product deposited is sufficient to correctly cover the wound.

A subject matter of the present invention is thus a fluid composition intended to be applied to the skin, comprising a cellulose derivative, a vegetable oil and a solvent for said derivative which is volatile, characterized in that the cellulose derivative represents from 6% to 12% by dry weight of the total weight of the composition, in that the vegetable oil represents from 5% to 15% by weight of the total weight of the composition and in that the oil/cellulose ratio by weight, by dry weight, is between 0.8 and 1.5.

The cellulose derivative can be chosen from nitrocellulose, hydroxypropylmethylcellulose, hydroxypropylcellulose, ethylcellulose, cellulose esters and their mixtures.

The cellulose esters can be chosen from cellulose acetates, propionates, butyrates, isobutyrates, acetate/butyrates or acetate/propionates and their mixtures.

According to one embodiment, the polymer is a nitrocellulose. The nitrocellulose is preferably chosen from nitrocelluloses of high viscosity, in particular nitrocelluloses having a grade between RS 1/2 and RS 20 seconds according to the United States of America standard, which corresponds to a grade of between 8E and 21E according to the European standard. Preference is given, for example, to nitrocellulose of 10E or 11E grade according to the European standard, corresponding to the RS 15 seconds grade according to the United States of America standard.

The nitrocellulose can be chosen in particular from the RS 5 sec. and RS 15 sec. nitrocelluloses sold by Hercules, the DHL® 120/170, DHL® 25/45 or DHX® 40/70 products sold by Nobel Enterprises, the E 840® and E 620® nitrocelluloses produced by Wolff Cellulosics, and the products sold under the references E80®, E70®, E60® and E40® by SNPE-Bergerac.

The nitrocellulose can be supplied in the dry form or in solution in a solvent, such as isopropanol or ethanol.

The nitrocellulose is preferably present in a content ranging from 6% to 13% by dry weight, preferably from 9% to 11% by dry weight, for example between 9.5% and 10.5% by dry weight, with respect to the total weight of the composition.

The molecular weight Mw of the nitrocellulose is advantageously between 60,000 and 80,000.

Vegetable oil is understood to mean an oil resulting from a vegetable source, which has been subjected to additional refining and/or purification treatments, or also a chemical transformation, such as esterification, hydrogenation, peroxidation or etherification with another chemical compound or another natural fatty substance, for example.

The vegetable oil is advantageously chosen from sesame oil, castor oil, almond oil, canola oil, hazelnut oil, pistachio oil, linseed oil, borage oil, hemp oil, jojoba oil, sunflower oil, wheat germ oil, corn oil and/or corn germ oil, peanut oil, avocado oil, safflower oil, rapeseed oil, olive oil, argan oil, grape seed oil, soybean oil, walnut oil, cucumber seed oil, palm oil, coconut oil and their mixtures.

The oil can also be a derivative of one of the abovementioned vegetable oils. It can be a hydrogenated or nonhydrogenated or peroxidized or nonperoxidized oil.

It is advantageously soluble in the solvent of the composition.

The amount of oil, in particular of castor oil, represents, for example, from 5% to 15% by weight, with respect to the total weight of the composition, advantageously from 5% to 12% by weight, preferably from 8% to 12% by weight and more preferably from 9.5% to 10.5% by weight, with respect to the total weight of the composition.

The oil and the nitrocellulose can be present in the composition according to the invention in an oil:nitrocellulose ratio by weight (by dry weight) of between 0.8 and 1.5, or even between 0.9 and 1.25, more particularly of the order of 1.

The compositions of the invention can also comprise a volatile solvent which dissolves the cellulose derivative. This solvent makes it possible to dissolve a portion or all of the ingredients of the composition and participates in the formation of a film on the skin during the application thereof.

In the context of the present invention, volatile solvent is understood to mean a solvent capable of rapidly evaporating on contact with the skin. Water is excluded from this definition. Preference is given to volatile nonaqueous solvents or mixtures of volatile nonaqueous solvents, the boiling point of which is greater than 50° C. (at atmospheric pressure).

Mention may be made, as volatile solvent which can be used in the context of the present invention, of:

- ketones, such as methyl ethyl ketone, methyl isobutyl ketone, diisobutyl ketone, isophorone, cyclohexanone or acetone;
- alcohols, such as ethanol, isopropanol, n-propanol, n-butanol, diacetone alcohol, 2-butoxyethanol or cyclohexanol;
- glycols, such as ethylene glycol, propylene glycol, pentylene glycol or glycerol;
- propylene glycol ethers, such as propylene glycol monomethyl ether, propylene glycol monomethyl ether acetate or dipropylene glycol mono(n-butyl) ether;
- esters, such as ethyl acetate, methyl acetate, propyl acetate, n-butyl acetate or isopentyl acetate;
- ethers, such as diethyl ether, dimethyl ether or dichlorodiethyl ether; and
- their mixtures.

The volatile solvent will advantageously be chosen from ethanol, ethyl acetate and their mixtures. According to one embodiment, the volatile solvent is a mixture of ethyl acetate and ethanol, preferably in proportions by weight of between 1/1 and 3/1, preferably of the order of 2/1.

Preference is given to solvents or solvent mixtures having a rate of evaporation which is less than that of the ethers. It will be possible to choose solvents or solvent mixtures having an evaporation profile which is close to that of the abovementioned mixture of ethyl acetate and ethanol.

This is because the applicant company has found that the composition spreads better when the volatile solvent has a rate of evaporation lower than that of an alcohol/ether (25/75 volume/volume) mixture as described in the prior art.

The amount of volatile solvent represents, for example, from 60% to 90% by weight, with respect to the total weight of the composition, advantageously from 70% to 90% by weight, with respect to the total weight of the composition.

The composition is essentially devoid of water. It preferably comprises less than 2% by weight thereof.

In one embodiment, the composition comprises from 9% to 11% by dry weight of nitrocellulose, from 9% to 11% by weight of castor oil, and a mixture of a volatile ester and of a volatile alcohol.

The compositions according to the invention can also comprise additives normally used in the preparation of dressings, such as fragrances, preservatives, depigmenting agents, antibacterial agents, antifungal agents, healing agents, pain killers, anti-inflammatories, hydrating agents, keratolytic agents, vitamins, glycerol or citric acid.

Generally, the active agents are chosen from:

- antibacterials, such as polymyxine B, penicillins (amoxicillin), clavulanic acid, tetracyclines, minocycline, chlortetracycline, aminoglycosides, amikacin, gentamycin, neomycin, silver and its salts (silver sulfadiazine), or probiotics;
- antiseptics, such as thiomersal, eosin, chlorhexidine, phenylmercuric borate, aqueous hydrogen peroxide solution, Dakin's solution, triclosan, biguanide, hexamidine, thymol, Lugol's solution, iodinated povidone, merbromin, benzalkonium chloride, benzethonium chloride, ethanol or isopropanol;
- antivirals, such as aciclovir, famciclovir, ritonavir;
- antifungals, such as polyenes, nystatin, amphotericin B, natamycin, imidazoles (miconazole, ketoconazole, clotrimazole, econazole, bifonazole, butoconazole, fenticonazole, isoconazole, oxiconazole, sertaconazole, sulconazole, thiabendazole, tioconazole), triazoles (fluconazole, itraconazole, ravuconazole, posaconazole, voriconazole), allylamines, terbinafine, amorolfine, naftifine or butenafine;
- flucytosine (antimetabolite), griseofulvin, caspofungin or micafungin;
- pain killers, such as paracetamol, codeine, dextropropoxyphene, tramadol, morphine and its derivatives, or corticoids and derivatives;
- anti-inflammatories, such as glucocorticoids, nonsteroidal anti-inflammatories, aspirin, ibuprofen, ketoprofen, flurbiprofen, diclofenac, aceclofenac, ketorolac, meloxicam, piroxicam, tenoxicam, naproxen, indomethacin, naproxcinod, nimesulide, celecoxib, etoricoxib, parecoxib, rofecoxib, valdecoxib, phenylbutazone, niflumic acid, mefenamic acid or 18β-glycyrrhetinic acid;
- active agents which promote healing, such as retinol, vitamin A, vitamin E, N-acetylhydroxyproline, *Centella Asiatica* extracts, papain, silicones, essential oils of thyme, of niaouli, of rosemary and of sage, hyaluronic acid, synthetic polysulfated oligosaccharides having from 1 to 4 monosaccharide units, such as the potassium salt of octasulfated sucrose, the silver salt of octasulfated sucrose or sucralfate, or allantoin;
- depigmenting agents, such as kojic acid (Kojic Acid SL®—Quimasso (Sino Lion)), arbutin (Olevatin®—Quimasso (Sino Lion)), the mixture of sodium palmitoylproline and European water lily extract (Sepicalm®—Seppic), undecylenoylphenylalanine (Sepiwhite®—Seppic), the licorice extract obtained by fermentation of *Aspergillus* and ethoxydiglycol (Gatuline Whitening®—Gattefossé), octadecenedioic acid (ODA White®—Sederma), α-arbutin (Alpha-arbutin®, SACI-CFPA (Pentapharm)), the aqueous extract of *Arctostaphylos uva-ursi* leaves (Melfade-J®—SACI-CFPA (Pentapharm)), the complex plant mixture Gigawhite® (SACI-CFPA (Alpaflor)), diacetylboldin (Lumiskin®—Sederma), the satsuma extract (Melaslow®—Sederma), the mixture of lemon extract enriched in citric acid and of cucumber extract (Uninontan U-34—Unipex), the mixture of *Rumex occidentalis* extract and of vitamin C (Tyrostat® 11—Unipex), oligopeptides (Melanostatin 5®—Unipex), kojic dipalmitate (KAD-15®—Quimasso (Sino Lion)), the complex of natural origin Vegewhite® from LCW, wheat germ extracts (Clariskin® II—Silab) or ethylenediamine-triacetate (EDTA);

keratolytic agents, such as salicylic acid, zinc salicylate, ascorbic acid, α-hydroxylated acids (glycolic, lactic, malic, citric or tartaric acid), silver maple, sour cherry or tamarind extracts, urea, the topical retinoid Keratoline® (Sederma), the proteases obtained by fermentation of *Bacillus subtilis*, the product Linked-Papain® (SACI-CFPA) or papain (proteolytic enzyme resulting from the papaya fruit);

restructuring active agents (for example restructuring active agents for superficial body growths), such as silica derivatives, vitamin E, camomile, calcium, horsetail extract or silk lipester;

sunscreens, such as chemical screening agents (oxybenzone, sulisobenzone, dioxybenzone, Tinosorb S®, avobenzone, 2-ethoxyethyl p-methoxycinnamate, Uvinul® A+, Mexoryl® XL, octyl methoxycinnamate or octinoxate, octyl salicylate or octisalate, octyl triazone or Uvinul® T 150, methyl salicylate, meradimate, enzacamene, MBBT or Tinosorb® M, octyl cyanophenylcinnamate or Parsol® 340, para-aminobenzoic acid, ensulizole, Parsol® SLX or polysiloxane-15 or benzylidene malonate polysiloxane, triethanolamine salicylate or trolamine salicylate, Mexoryl® SX or terephthalylidene dicamphor sulfonic acid) and inorganic screening agents (zinc oxides, titanium dioxide, kaolin or ichthyol);

anesthetics, such as benzocaine, lidocaine, dibucaine, pramoxine hydrochloride, bupivacaine, mepivacaine, prilocaine or etidocaine.

The composition according to the invention can also comprise flavorings or bitterness agents (such as denatonium benzoate).

As indicated above, the composition according to the present invention is provided in the form of a fluid liquid intended to be applied using an appropriate applicator, such as a brush or a palette knife.

The compositions according to the present invention are intended to be applied to wounds or scars, whether related to an accident, a disease or the consequences of a surgical operation, or burns. These compositions can also be applied to any skin ailment. Mention may be made, by way of example, of acne, chickenpox, shingles, blotches, first degree burns, eczema, hyperpigmentation, sunlight eruption, vitiligo, xerosis, prophyria, stretch marks, psoriasis or insect bites or stings.

A subject matter of the invention is thus the composition as defined above for the use thereof in the protection of burns, in particular minor burns, superficial skin wounds, or scars. The compositions according to the invention are also of use in the treatments of blisters, chaps or cracks. The composition according to the present invention can also be applied to incompletely healed wounds provided that they are not oozing and that they have decontaminated beforehand.

The invention also relates to the use of a composition as defined above in the preparation of a dressing intended to be protect burns, superficial skin wounds, or scars.

The following examples illustrate the invention without limiting the scope thereof.

EXAMPLE 1

The following composition is prepared.

| Commercial name | Manufacture/Supplier | INCI name | CAS No. | % by weight |
|---|---|---|---|---|
| 1. DHL ® 120/170 IPA | Nobel | Nitrocellulose | 9004-70-0 | 11.5 |
| 2. Castor oil | Prod'hyg Laboratoire | *Ricinus Communis* (Castor) Seed Oil | 8001-79-4 | 10.0 |
| 3. Absolute ethanol | Charbonneau Brabant | Alcohol | 64-17-5 | 25.7 |
| 4. Ethyl acetate | Darfeuille | Ethyl acetate | 141-78-6 | 51.3 |
| 5. Enoxolone ® PH | Cognis | 18β-Glycyrrhetinic acid | 471-53-4 | 1.5 |

Procedure:

The ingredients 2 to 5 are mixed with stirring at 700 revolutions/min for 10 minutes with a propeller mixer. The nitrocellulose is subsequently dispersed in the mixture with stirring, and the mixture is successively stirred at 1100 revolutions/min for 20 minutes and 2000 revolutions/min for 30 minutes.

Retention Test:

The tests are carried out on 13 people for 24 h after just one application, under the following conditions:
- the film-forming composition is deposited on the forehead, the top of the hand and the waist
- showering is obligatory at T12h and optional at T24
- the evaluations are carried out at T6h, T12h (before showering and after showering) and T24h

| | Results as % detached (means) | | |
|---|---|---|---|
| Means | Film-forming composition forehead | Film-forming composition hand | Film-forming composition waist |
| Detachments T6h | 1.5 | 3.8 | 9.2 |
| Detachments T12h | 3.0 | 4.6 | 20.0 |
| Detachments T12h after showering | 8.4 | 6.1 | 28.4 |
| Detachments T24h | 29.2 | 7.6 | 36.9 |

| | Maximum detachments observed (as %) | | |
|---|---|---|---|
| | Film-forming composition forehead | Film-forming composition hand | Film-forming composition waist |
| Detachments T6h | 10.0 | 20.0 | 30.0 |
| Detachments T12h | 20.0 | 20.0 | 60.0 |
| Detachments T12h after showering | 50.0 | 20.0 | 80.0 |
| Detachments T24h | 90.0 | 20.0 | 80.0 |

The retention of the film-forming composition on the hand is greater than the retention of the film-forming composition on the forehead and the waist, this being despite washing of hands. The composition according to the invention thus has a good resistance to water.

From the point where it has been worn for T6h, the film-forming composition applied to the waist is significantly more detached than on the areas of the hands and forehead. The detachment of the film-forming composition on the forehead is doubtless promoted by the rubbing actions of the sheets during the night since it changes from 8% on average at T12h after showering to approximately 30% on average at T24h.

The film-forming composition on the hand does not exhibit significant detachments at T24h.

COMPARATIVE EXAMPLE 2

Product Filmogel® Crevasses

The composition of example 1 is spread uniformly and in calibrated fashion over an inert support and is then left to dry in order for the volatile solvent to evaporate. A film with a thickness of 30 microns is obtained, which film is separated from the support.

Test specimens of 15×50 mm (corresponding to a surface area of 7.5 cm$^2$) are cut out for the evaluation. They are subjected to drawing, by a dynamometer, which will measure the length of maximum elongation before breaking and the force necessary.

The same test specimens are prepared with the product Filmogel® Crevasses.

The results obtained are:
Filmogel® Crevasses=43% elongation Force necessary=14 N/cm
Our formulation=115% elongation Force necessary=7 N/cm The formulation according to the invention is thus more flexible.

The Filmogel® Crevasses spreads less easily as it is more viscous and does not comprise much plasticizer; for this reason, it exhibits less slip. The film formed with Filmogel® Crevasses is thicker and less flexible. Consequently, the film is more brittle and less comfortable.

COMPARATIVE EXAMPLE 3

| Commercial name | Manufacture/ Supplier | INCI name | CAS No. | % by weight |
|---|---|---|---|---|
| 1. DHL ® 120/170 IPA | Nobel | Nitrocellulose | 9004-70-0 | 17.6 |
| 2. Castor oil | Prod'hyg Laboratoire | *Ricinus Communis* (Castor) Seed Oil | 8001-79-4 | 15.3 |
| 3. Absolute ethanol | Charbonneau Brabant | Alcohol | 64-17-5 | 21.6 |
| 4. Ethyl acetate | Darfeuille | Ethyl acetate | 141-78-6 | 43.3 |
| 5. Parsol ® 1789 | DSM | Butyl Methoxydibenzoyl-methane | 70356-09-1 | 1.0 |
| 6. Parsol ® MCX | DSM | Ethylhexyl Methoxycinnamate | 5466-77-3 | 1.2 |

Procedure:

The ingredients 2 to 5 were mixed with stirring at 700 revolutions/min for 10 minutes with a propeller mixer. The nitrocellulose was subsequently dispersed in the mixture with stirring and the mixture was successively stirred at 1100 revolutions/min for 20 minutes and at 2000 revolutions/min for 30 minutes.

The nitrocellulose content of comparative example 3 is 14.1% by dry weight. The composition according to example 3 was very viscous and stringy, which made it difficult to spread with a brush. Furthermore, the film formed by this composition took a long time to dry and was not even. Thus, if an active agent/active agents or a sunscreen/sunscreens is/are added to this type of composition, the amount of active agent(s) which is available or the antisun protection is not uniform.

The invention claimed is:

1. A bottle having an applicator, said bottle containing a fluid composition suitable for direct application to skin or wounds, said composition comprising a cellulose derivative, a vegetable oil and a volatile solvent for said cellulose derivative, wherein the cellulose derivative represents from 6% to 13% by dry weight of the total weight of the composition, wherein the vegetable oil represents from 5% to 15% by weight of the total weight of the composition and wherein the vegetable oil/cellulose derivative ratio by dry weight, is between 0.8 and 1.5,
   wherein the cellulose derivative is a nitrocellulose, and
   wherein the vegetable oil is castor oil.

2. The bottle as claimed in claim 1, wherein the solvent for said cellulose derivative represents between 70% and 90% by weight of the total weight of the composition.

3. The bottle as claimed in claim 1, wherein the solvent for said cellulose derivative is selected from the group consisting of ethanol, ethyl acetate and their mixtures.

4. The bottle as claimed in claim 1, wherein the composition comprises nitrocellulose, castor oil, ethyl acetate and ethanol.

5. The bottle as claimed in claim 1, wherein the composition additionally comprises an ingredient selected from the group consisting of depigmenting agents, antibacterial agents, antifungal agents, healing agents, pain killers, anti-inflammatories, hydrating agents, keratolytic agents, vitamins, restructuring agents for superficial body growths, sunscreens and their mixtures.

6. The bottle as claimed in claim 1, wherein the composition is effective for the protection of burns, wounds, scars or skin ailments.

7. The bottle as claimed in claim 1, wherein the vegetable oil represents from 9.5% to 10.5% by weight of the total weight of the composition.

8. The bottle as claimed in claim 1, wherein the applicator is selected from the group consisting of a brush and a spatula.

9. The bottle as claimed in claim 1, wherein the additional ingredient in the composition is a sunscreen.

* * * * *